(12) United States Patent
Fraser

(10) Patent No.: US 9,778,239 B2
(45) Date of Patent: Oct. 3, 2017

(54) IN-BOTTLE DETECTION METHOD

(71) Applicant: UNIVERSITY OF LEICESTER, Leicester (GB)

(72) Inventor: George William Fraser, Leicester (GB)

(73) Assignee: University of Leicester, Leicestershire (GB)

( * ) Notice: Subject to any disclaimer, the term of this patent is extended or adjusted under 35 U.S.C. 154(b) by 0 days.

(21) Appl. No.: 15/303,999

(22) PCT Filed: Mar. 18, 2015

(86) PCT No.: PCT/GB2015/050787
§ 371 (c)(1),
(2) Date: Oct. 13, 2016

(87) PCT Pub. No.: WO2015/159043
PCT Pub. Date: Oct. 22, 2015

(65) Prior Publication Data
US 2017/0030881 A1 Feb. 2, 2017

(30) Foreign Application Priority Data

Apr. 15, 2014 (GB) .................................. 1406707.8

(51) Int. Cl.
*G01J 3/00* (2006.01)
*G01N 33/14* (2006.01)
(Continued)

(52) U.S. Cl.
CPC ........... *G01N 33/146* (2013.01); *G01N 21/31* (2013.01); *G01N 21/33* (2013.01); *G01N 21/90* (2013.01); *G01N 21/9027* (2013.01)

(58) Field of Classification Search
CPC ........ G01N 33/14; G01N 21/90; G01N 21/33; G01N 33/146; G01N 21/9027;
(Continued)

(56) References Cited

U.S. PATENT DOCUMENTS 5,753,511 A 5/1998 Selinfreund
7,840,360 B1 11/2010 Micheels et al.
(Continued)

FOREIGN PATENT DOCUMENTS

CN 101256143 9/2008
CN 103645144 3/2014
(Continued)

OTHER PUBLICATIONS

Pisani, Francesca "International Search Report and Written Opinion—International Application No. PCT/GB2015/050787" May 18, 2015; European Patent Office as ISA; pp. 1-9.

*Primary Examiner* — Jamil Ahmed
(74) *Attorney, Agent, or Firm* — Nicholas J. Landau; Bradley Arant Boult Cummings LLP

(57) ABSTRACT

This invention relates to a method for analyzing a liquid when inside a container in order to detect counterfeiting or adulteration of the liquid, the container being at least partially transparent to visible light. The method comprises the steps of: (a) measuring a first transmission spectrum through the container and the liquid at a first orientation of the container which defines a first optical path length through the liquid, (b) measuring a second transmission spectrum through the container and the liquid at a second orientation of the container which defines a second optical path length through the liquid, the second optical path length being different from the first optical path length, and the second spectrum at least partially overlapping with the first spectrum, (c) calculating the ratio ($R(\lambda)$) of the first and second spectral intensities at each wavelength in the area of overlap, and (d) comparing this ratio ($R(\lambda)$) to a reference measurement of the ratio for a non-counterfeit and unadulterated sample of the liquid being tested.

9 Claims, 7 Drawing Sheets

(51) Int. Cl.
*G01N 21/31* (2006.01)
*G01N 21/33* (2006.01)
*G01N 21/90* (2006.01)

(58) Field of Classification Search
CPC ........ G01N 21/49; G01N 15/06; G01N 21/00; G01N 33/03; G01N 21/3504; G01N 2021/3185; G01N 21/64; G06F 17/18; G01R 27/28; G01R 23/00; G01J 3/00; G01J 3/42

See application file for complete search history.

(56) References Cited

U.S. PATENT DOCUMENTS

| | | |
|---|---|---|
| 2001/0055115 A1 | 12/2001 | Garver |
| 2004/0000653 A1* | 1/2004 | Nordlund ............... G01N 21/31 250/573 |
| 2008/0218733 A1* | 9/2008 | Benes ....................... G01J 3/02 356/51 |
| 2011/0184681 A1 | 7/2011 | Augustine et al. |

FOREIGN PATENT DOCUMENTS

| | | |
|---|---|---|
| EP | 2071320 | 6/2009 |
| GB | 2297377 | 7/1996 |
| WO | 0233404 | 4/2002 |
| WO | 2014138136 | 9/2014 |

* cited by examiner

IN-BOTTLE DETECTION METHOD

CROSS-REFERENCE TO RELATED APPLICATIONS

This application is a national stage under 35 U.S.C. 371 of International Application PCT/GB2015/050787, filed on Mar. 18, 2015 (currently published). International Application PCT/GB2015/050787 cites the priority of British Patent Application No. 1406707.8, filed Apr. 15, 2014.

This invention relates to a method for analysing a liquid when inside a container, where the container is at least partially transparent to visible light. The method can be applied to many fields, but finds particular use in the detection of counterfeit or adulterated alcoholic beverages, for example whisky.

Estimates for the revenue and taxation losses to industry and government arising from the counterfeiting of Scotch whisky are of necessity inexact, but are certainly of sufficient scale to make authentication a high priority. A number of techniques have been used in attempts to discriminate real from fake whiskies and to detect the watering down of authentic brands. These include:
  (a) Broad-band optical spectroscopy,
  (b) Raman and near-infrared (NIR) spectroscopy, concentrating on the complex molecular bonding within the liquid, and
  (c) Mass spectrometry, measuring the mass abundances of the constituent molecules.

To date, however, it has not been possible to provide a portable instrument capable of "in the field" testing with high reliability without breaking the seal of the container to remove a sample for analysis (for example, opening the bottle of whisky being analysed). The industry standard technology for authentication remains gas chromatography carried out in a central analytical laboratory.

This invention seeks to address this problem through the use of optical spectroscopy in transmission, rather than in reflectance, mode to provide the basis for an "in the bottle" and "in the field" screening test, for example as a screening test for the authenticity of whisky and other high value liquors.

This invention relates to method for analysing a liquid when inside a container in order to detect counterfeiting or adulteration of the liquid, the container being at least partially transparent to visible light, the method comprising the steps of:
  (a) measuring a first transmission spectrum through the container and the liquid at a first orientation of the container which defines a first optical path length through the liquid,
  (b) measuring a second transmission spectrum through the container and the liquid at a second orientation of the container which defines a second optical path length through the liquid, the second optical path length being different from the first optical path length, and the second spectrum at least partially overlapping with the first spectrum,
  (c) calculating the ratio of the first and second spectra in the area of overlap, and
  (d) comparing this ratio to a reference measurement of the ratio for a non-counterfeit and unadulterated sample of the liquid being tested.

An important advantage of the method of the present invention is that it allows the liquid inside a container to be analysed without the container needing to be opened. This is particularly important when analysing alcoholic beverages in bottles because, once opened, these products cannot be sold. In some embodiments, the container is sealed (eg it is closed).

In the context of this invention, the term "adulteration" is used to mean the addition of a foreign substance to the liquid being tested. An example of adulteration is the addition of water to the liquid, for example to a whisky. Also in the context of this invention, the term "counterfeit" is used to refer to a liquid which is presented (for example, for sale) as being something other than what it actually is. Examples of counterfeiting include misrepresenting a blended whisky as a malt whisky, or misrepresenting a mixture of ethanol and a caramel colourant as a whisky. In some embodiments, the first and second spectra are selected such that they are suitable for detecting a suspected type of adulteration or counterfeiting. The term "area of overlap" is used to mean the parts of the wavelength range of the first and second spectra which overlap. In step (c), calculating the ratio of the first and second spectra preferably comprises calculating the ratio ($R(\lambda)$) of the first and second spectral intensities at each wavelength in the area of overlap.

Preferably, the container comprises glass or plastic.

It is preferred that the liquid comprises alcohol (preferably ethanol), preferably that it is an alcoholic (preferably ethanolic) beverage. The alcoholic beverage may comprise one or more of the following: vodka, gin, cognac, brandy, bitters, rum, tequila, whisky or wine. However, the method of this invention is applicable to non-alcoholic beverages, as well as to other alcoholic beverages. Preferably, the alcoholic beverage is a coloured alcoholic beverage (ie it is not clear). Preferred coloured alcoholic beverages include cognac, brandy, bitters, dark rum, tequila, whisky and wine.

The term "spectrum" is used to refer to measurements at at least two different wavelengths. In general, in order to obtain the best possible data from the method of the invention it is preferable to obtain a spectrum comprising as many readings as possible across as broad a wavelength range as possible. However, it is possible to distinguish adulterated/counterfeit from unadulterated/non-counterfeit liquids with fewer readings and using narrower wavelength ranges. Once the skilled person is aware of how to detect a particular type of counterfeiting and/or adulteration using the method of the invention, determining the number of readings and the wavelength range required to detect that type of adulteration/counterfeiting of a particular liquid would be a matter of routine experimentation.

In some embodiments, the first and/or second spectra include measurements made across the wavelength range 350-500 nm. Preferably, the first and/or second spectra include measurements made across the wavelength range of 300-600 nm, more preferably 300-750 nm, even more preferably 300-850 nm. Preferably, the wavelength range of the first and second spectra is substantially identical.

Preferably, the transmission spectrum is measured using a light source, more preferably a white light source (ie comprising a mixture of wavelengths in the visible range). In some embodiments, the white light source is a halogen lamp. Preferably, the transmission spectrum is measured using a light source comprising one or more optical fibres.

The reference measurement may be stored electronically (for example on a hard disk), and may be stored either locally (eg with respect to the place of the first and second spectral measurements, such as within the spectrometer being used to make the measurements) or accessed remotely (eg from a remote server).

This invention will be further described by reference to the following Figures which are not intended to limit the scope of the invention claimed, in which:

A detailed description of one embodiment of the method of this invention is set out below.

A broad-band optical source (for example one or more optical fibres connected to a halogen light source) with an intensity $I(\lambda)\,d\lambda$ photons·cm$^{-2}$·s$^{-1}$ in the wavelength interval $\lambda$, $\lambda+d\lambda$ is used to illuminate an at least partially transparent (normally glass or plastic) bottle through a small contact aperture of area $dA$. Contact with the bottle on the entrance (ie of light from the source) and exit (ie of light from the bottle to the detector) surfaces may be conveniently established using one or more (ie single or bundled) optical fibres. The optical fibres are mounted so as to exclude ambient light.

Figure 1:
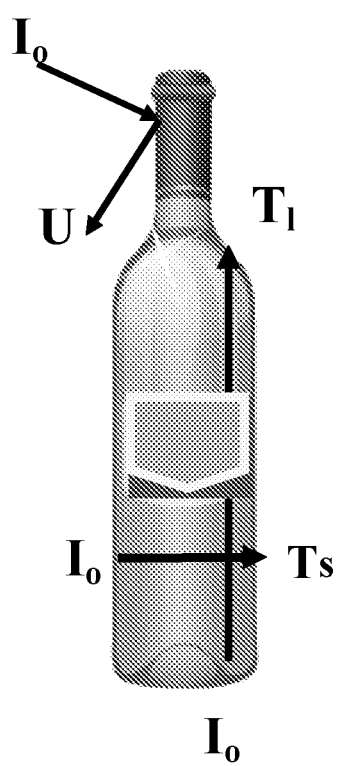
FIG. 1 shows an example of a bottle containing a liquid for analysis according to one embodiment of the invention.

A bottle (ie a container) containing a liquid for analysis according to the method of the invention is shown in FIG. 1. Three different directions of incident light are indicated with arrows and the letter I. Incident light I shone at the opaque bottle cap indicated at the top of the bottle of FIG. 1 is reflected as indicated by reflected light arrow U. In relation to the method of the invention, the other two incident light beams I are shone at two different orientations through the at least partially transparent parts of the bottle. This light at least partially passes through the bottle and the liquid contained in the bottle, as shown by transmitted light T, so that it reaches a detector on the opposite side of the bottle from the source. In this way, two different source-detector axes are defined. In FIG. 1, the two axes are a longer vertical axis and a shorter horizontal axis.

If transmission measurements are made for two orientations of the bottle (ie two different source-detector axes, through the at least partially transparent parts of the bottle), as indicated in FIG. 1, then the transmitted fluxes T for the two orientations are:

$$T_s(\lambda) = t_{glass}(\lambda) \cdot t_{whisky}(\lambda, d_s) \cdot Q(\lambda) \cdot I(\lambda) dA + N_d \quad (1a)$$

and $$T_l(\lambda) = t_{glass}(\lambda) \cdot t_{whisky}(\lambda, d_l) \cdot Q(\lambda) \cdot I(\lambda) dA + N_d \quad (1b)$$

where $d_s$ and $d_l$ are, respectively, the lengths of the shorter and the longer of two optical paths through the bottle. In the above equation, $t_{glass}(\lambda)$ is the optical absorbance of the glass bottle, $t_{whisky}(\lambda, d_s)$ is the optical absorbance of the whisky through the shorter optical path through the bottle and $t_{whisky}(\lambda, d_l)$ is the optical absorbance of the whisky through the longer optical path through the bottle. $Q(\lambda)$ denotes the optical quantum efficiency (counts per incident photon) of the spectrometer which detects the transmitted flux, combining both detector and wavelength-dispersive element (ie grating) contributions.

If the walls of the bottle are effectively of constant thickness and/or very highly transparent, the terms describing the glass transmission can effectively be "divided out". Then, provided the signal level in both orientations is much greater than the background count rate $N_d$, the ratio:

$$R(\lambda) = T_s/T_l \quad (2)$$

is a property of the bottle geometry ($d_s$ and $d_l$) and of the whisky's optical absorbance only. According to Mackenzie and Aylott (Analyst 129 (2004) 607-612), whisky is very strongly absorbing in the ultraviolet band 200-400 nm, with absorbances exceeding 50%, even for path lengths as small as 1 mm. Thus, we can anticipate that, for a given bottle geometry, there will be a minimum working wavelength below which eq. (2) will become the uninformative division of one background count rate by another. This can be determined by the skilled person using routine experimentation on the sample being tested.

Although the ratio $R(\lambda)$ above can be measured without knowing the geometry of the bottle, a knowledge of the bottle geometry—described by the lengths $d_s$ and $d_l$—allows the estimation of the wavelength-dependent linear attenuation coefficient $\mu(\lambda)$—a property of the whisky in isolation;

$$\mu(\lambda) = \frac{\ln(R)}{d_l - d_s}\ \text{mm}^{-1} \quad (3)$$

Equations (2) and (3) are the basis for a comparative, rather than an analytical technique. The measurements obtained are compared to a database of known whisky "signature" measurements for $R(\lambda)$ and/or $\mu(\lambda)$.

The variance S:

$$S = \frac{1}{N} \sum_{1}^{N} \{(R_O(\lambda_i) - R(\lambda_i))^2\} \quad (4)$$

is used to quantify the difference between unknown (R) and reference ($R_O$) spectra. N is the number of measurements made. Table 1 below shows values of S calculated for N=594 points equally spaced between wavelength limits 400 nm and 600 nm.

EXAMPLES

An extensive sample set of whiskies was provided by the Scotch Whisky Research Institute (SWRI). This was supplemented by dilution and other trials on commercially-sourced blends and malts. The distinctive "signature" produced from "long" and "short" optical spectra measured after transmission of a quasi white light input source through two distinct liquid path lengths ($d_l$ and $d_s$, respectively) can be used to discriminate between "real" and "fake" material. This can also form the basis for a comparative (rather than analytical) field-deployable instrument.

The samples were analysed in all the examples below using a medium-performance portable spectrometer. For this analysis, a Hamamatsu type C10082CA Mini-Spectrometer based on a one dimensional, back-thinned, 2048-pixel CCD (charge coupled device) which was capable of providing better than 6 nm wavelength resolution in the 200-800 nm band (actually 164-845 nm) from a holographic grating ruled in quartz was used. The manufacturer's software was used to acquire all data. The spectral accumulation times were typically in the range 0.1-1 s. The roll-off in sensitivity at both the upper and lower limits of the bandpass was determined by the CCD, operating uncooled. The manufacturer's claimed temperature dependence of wavelength (0.04 nm/° C.) would provide excellent operational stability in a "field-portable" embodiment.

The 2048 channels of the Type C10082CA detector oversample the grating response by a factor:

~6 nm/[600 nm/2048]

or about 20 times. If added precision is required, therefore, binning-up pixels is an available tool, together with the co-adding of many individual spectra at full resolution. The data reported below consists mainly of individual 0.2 s spectra, smoothed by a "top-hat" or "box-car" filter 7 pixels (~2.3 nm) wide. The source of illumination used was a conventional halogen source with an effective temperature of 3100K and single optical fibres.

Example 1—Blended Whisky Spectra

Figure 2:
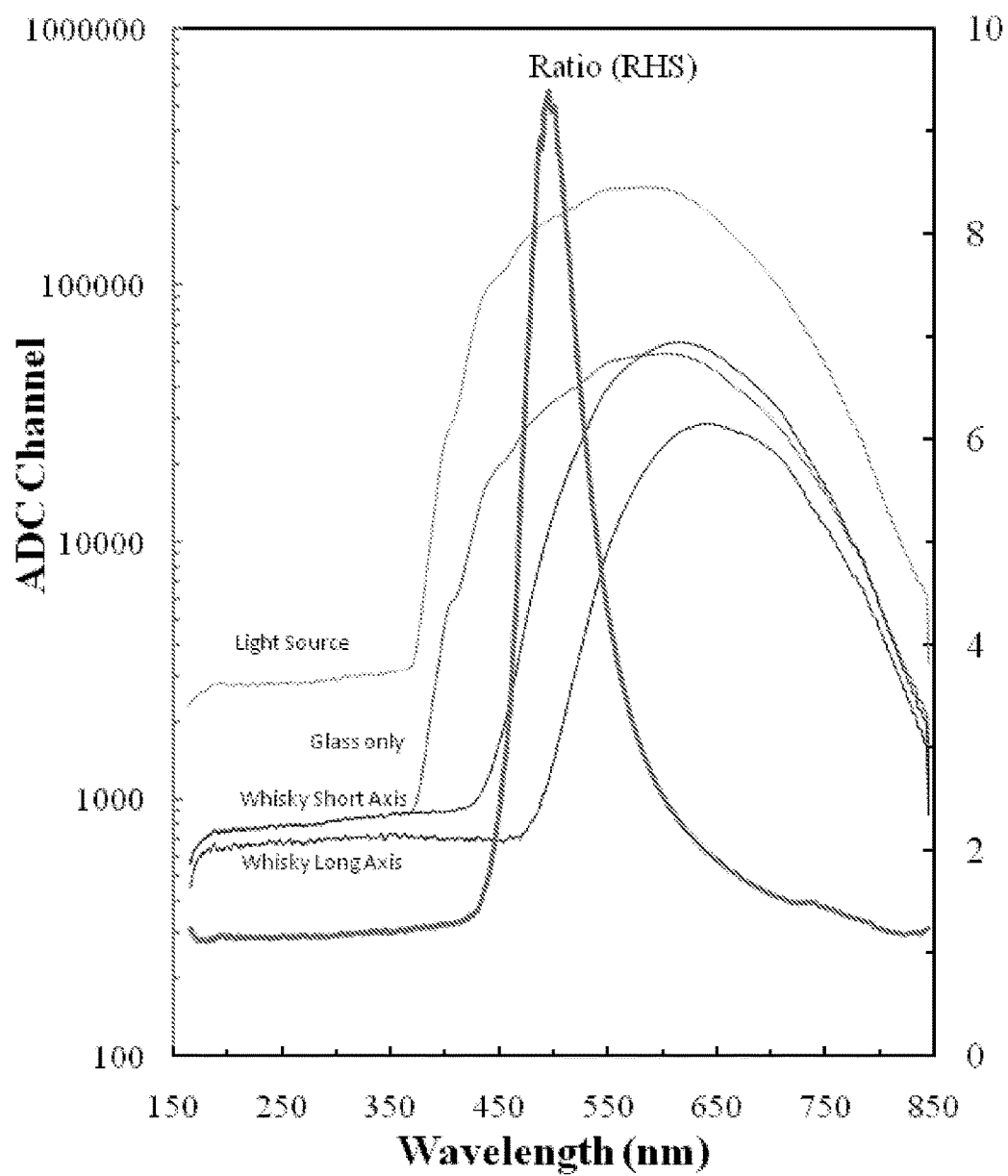
FIG. 2 shows an overlaid series of spectra obtained when analysing a blended whisky, as well as its R(λ) ratio (as defined in equation 2 below).

An initial series of measurements were made on a standard half-bottle (ie 350 ml) of supermarket own-brand blended whisky. The short axis (i.e. front-to-back of the bottle) path length was (43±1) mm and the long axis (i.e. side-to-side) path length was (87±1) mm FIG. 2 shows the overlaid spectra obtained over the range 350-850 nm resulting from:
  (1) The incident beam without any absorber or scatterer other than air (ie not passing through a sample), 10 ms accumulation time (labelled "Light Source"),
  (2) A view in transmission through the glass walls of the bottle when empty (ie the bottle only contains air), 50 ms accumulation time (labelled "Glass only"),
  (3) A view in transmission through the flat face of the bottle (the "short axis" of the whisky bottle, through the whisky in the bottle), 200 ms accumulation time (labelled "Whisky Short Axis"), and
  (4) A view in transmission through the full height of the bottle (the "long axis" of the whisky bottle, through the whisky in the bottle), 200 ms accumulation time (labelled "Whisky Long Axis").

The integration time for each spectrum was adjusted appropriately in the range 0.05-0.2 s in order to avoid saturation of the detected signals in the mid-range of wavelengths. While the "Light Source" spectrum ((1) above) and the "Glass only" transmission spectrum ((2) above) both extend down to 350 nm, the very high blue/UV absorption of the whisky itself suppresses values of R between 350 and 425 nm unless the background levels in the long and short axes are accounted for. In FIG. 2, this background correction was not carried out.

The left-hand axis of FIG. 2 is the signal strength for spectra (1)-(4). The ratio of spectra (3) and (4), ie the "short" and "long" whisky spectra, is shown in FIG. 2 as the derived spectrum "Ratio (RHS)". This spectrum uses the secondary, right-hand axis (the ratio $R(\lambda)$). In each case, the raw spectrum was smoothed using a ~3 nm wide top-hat filter.

In FIG. 2, the ratio $R(\lambda)$ for the whisky being analysed peaks at a value of about 9.5 at a wavelength of 500 nm. The derived linear absorption coefficient is $\mu=0.05$ mm$^{-1}$ at that wavelength. If, in absence of a two-channel (signal, signal plus background) capability in a one-dimensional sensor, the signal level in the first few detector pixels is averaged to give an estimate of the wavelength-independent background term $N_d$ (eqs. (1a,b)), R(500 nm) rises to ~30, corresponding to a linear absorption coefficient of 0.08 mm$^{-1}$.

Example 2—Measurement of Ratio $R(\lambda)$ of Diluted Whisky Samples

Figure 3:
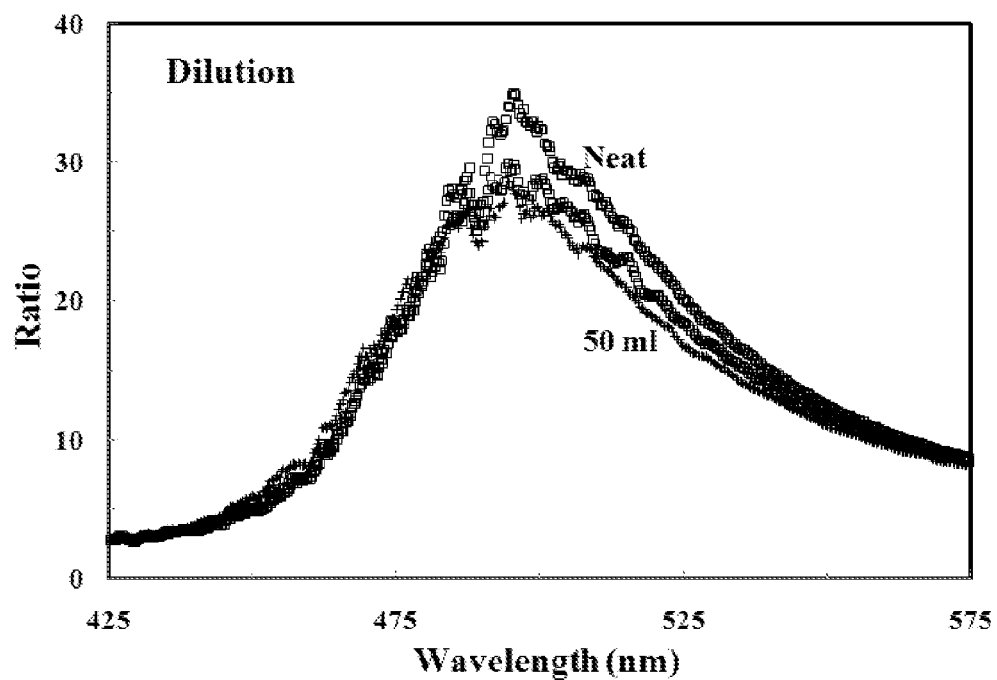
FIG. 3 shows overlaid measurements of the R(λ) ratio for three neat and diluted whisky samples.

The effects of successive dilution of an own-brand blend with distilled water were investigated using the background correction method described above involving averaging the first few detector pixels to give an estimate of $N_d$. Three samples were analysed (ie measuring "short" and "long" spectra to enable calculation of the ratio $R(\lambda)$) across the wavelength range 425-575 nm and the results are shown in FIG. 3. The samples tested were (i) an undiluted (ie neat) sample (square symbols), (ii) a first dilution where 50 ml of distilled water was added to 350 ml of neat whisky (circles), and (iii) a second dilution where 20 ml of distilled water was added to 350 ml of neat whisky (crosses).

The data in FIG. 3 shows that dilution with water is detectable using the method of the invention by a decrease in the peak (ie maximum) ratio value at a level of less than 15% v/v (i.e. 50 ml in 350 ml) and down to about 5% v/v (i.e. 20 ml in 350 ml). It is believed that there is no economic benefit to the counterfeiter in attempting dilution levels lower than 5% v/v.

Example 3—Measurement of Ratio $R(\lambda)$ of Ethanol, Water and Air-Filled Bottle of Example 2

Figure 4:
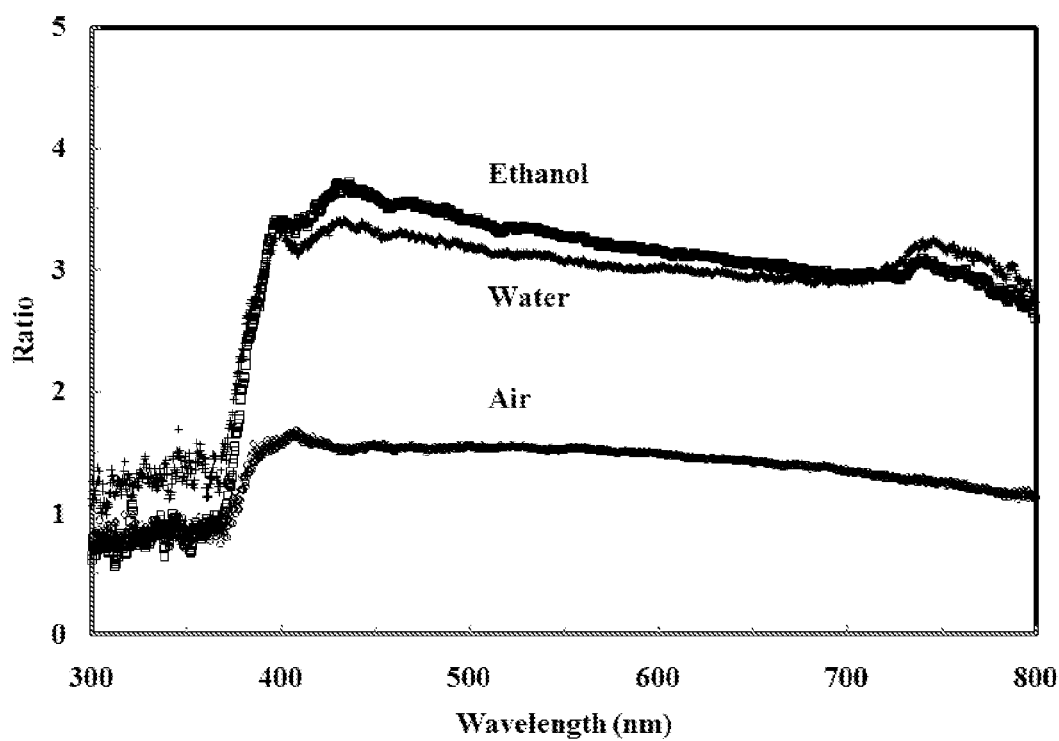
FIG. 4 shows overlaid measurements of the R(λ) ratio for ethanol, water and air in a container.

To confirm that the peak in the spectral ratio in FIG. 3 was due to the whisky content of the samples tested, the bottle was emptied and identical measurements made across the wavelength range 300-800 nm with the bottle filled with air, pure ethanol and distilled water respectively. The results are shown in FIG. 4. This figure shows the ratio $R(\lambda)$ for the air-filled bottle (circles), water-filled bottle (crosses) and ethanol-filled bottle (squares). The peak of the ratio $R(\lambda)$ for these three samples (~3.7 for the ethanol sample) is much lower than that of the whisky-containing samples of FIG. 3 (~35 for the neat sample).

According to the formulation of equation (2) a perfectly transparent medium should give a ratio value of unity, independent of wavelength. This ideal is approached for air-containing bottle of FIG. 4, for which R ~1.5 at 400 nm. The ratio $R(\lambda)$ then decreases slowly with increasing wavelength. This wavelength dependence suggests, for all three reference media of FIG. 4, that coherent scattering is the mechanism responsible for R not being unity; this also confirms that the highly-peaked $R(\lambda)$ curves presented in FIGS. 2 and 3 are a property of the whiskey under test and not (for example) of different bottle glass thicknesses in the two optical paths.

Example 4—Measurement of Ratio $R(\lambda)$ of Reference Sample Set

A further sample set was analysed using the same method (ie measuring "short" and "long" spectra to enable calculation of the ratio $R(\lambda)$). The compositions of this reference sample set are shown in Table 1 below. The reference set consisted of a number of Blends (labelled A, C, F and G), a Single Malt (labelled H) and approximations to them based largely on "neutral spirit" (i.e. an ethanol-water mixture) plus various additives, in particular the E150 family of caramels. The results of measurements on a subset of samples are shown in FIGS. 5-11. The samples were contained in clear plastic bottles which were smaller than conventional retail whisky bottles. The optical path length difference, dl–ds, of these smaller bottles was only 20 mm.

TABLE 1

| Sample Identifier | Basis | Additive | Statistic S |
|---|---|---|---|
| 1 | Neutral Spirit (40% ethanol in water) | None | |
| 3 | Neutral Spirit (40% ethanol in water) | E150a | |
| 4 | Neutral Spirit (40% ethanol in water) | E150b | |
| 5 | Neutral Spirit (40% ethanol in water) | E150c | |
| 6 | Neutral Spirit (40% ethanol in water) | E150d | 21.29 |
| 7 | 75% C(1) + 25% Sample 3 | — | 2.44 |
| 8 | 50% C(1) + 50% Sample 3 | — | 2.95 |
| 9 | 25% C(1) + 75% Sample 3 | — | 2.428 |
| 10 | C(1) | 2000 ppm sucrose | 0.387 |
| 11 | C(1) | 50 ppm vanillin | 0.757 |
| 12 | 50% C(1) + 50% Sample 3 | 6000 ppm methanol | 1.81 |
| 13 | Blend C, subjected to "forced fade" | — | 2.376 |
| Blend A | Blended whisky, single example | None | |
| Blend C | Blended whisky, four samples C(1)-C(4) | None | 0.061 0.37 0.058 0.104 |
| Blend F | Blended whisky, three samples F(1)-F(3) | None | |
| Blend G | Blended whisky, single example | None | |
| Malt H | Single malt whisky, single example | None | |

The degree of variability between the samples was tested. Variability could be due to (a) batch-to-batch variation in the production process or (b) non-reproducibility in the measurement process, for the authentic product.

Figure 5:
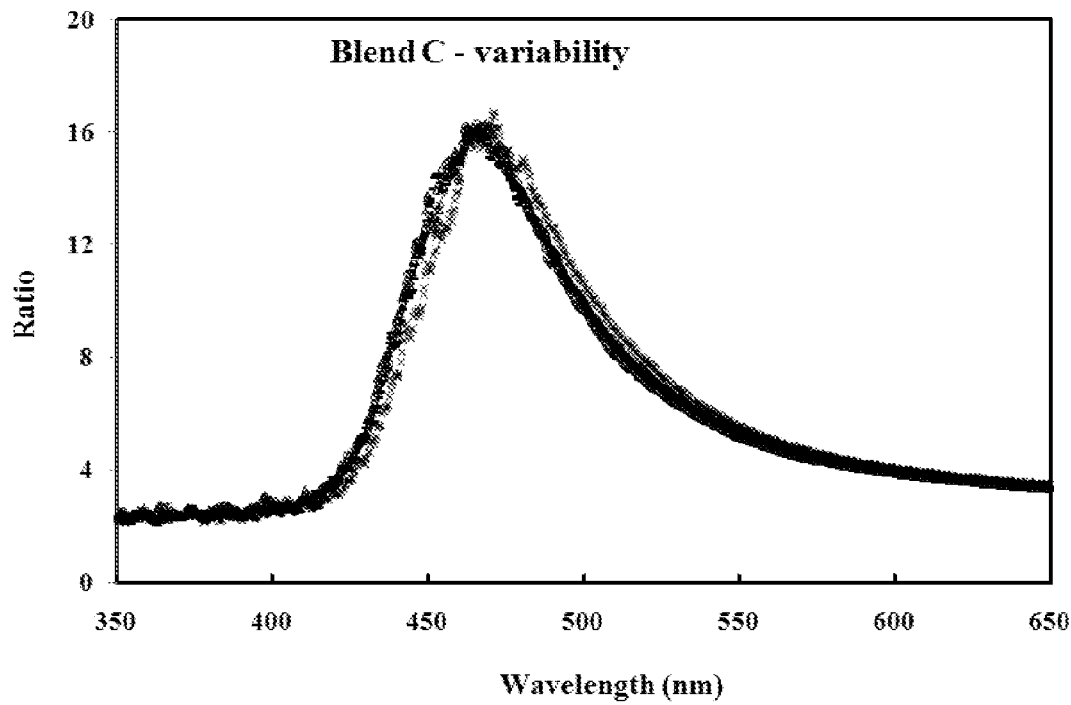
FIG. 5 shows overlaid measurements of the R(λ) ratio for four samples of Blend C.

FIG. 5 shows the degree of variation between the four available samples of Blend C. Samples from four different bottles of Blend C (labelled C1, C2, C3 and C4) were analysed in the wavelength range 350-650 nm. The proximity of the four traces in FIG. 5 shows that there is only minor variability in the ratio $R(\lambda)$ for the four samples (circle, square, cross and diamond).

As shown in Table 1 above, the difference in the parameter S between any one of the Blend C samples and the average for that population is less than ~0.1, with the exceptional value of 0.37 recorded for sample C(2). On that basis, every one of the eight counterfeit attempts except one—Sample 10, for which S equals 0.38—would be clearly classified as fake, and even Sample 10 would be flagged as lying right at the limit of the known variability of the authentic product.

Figure 6:
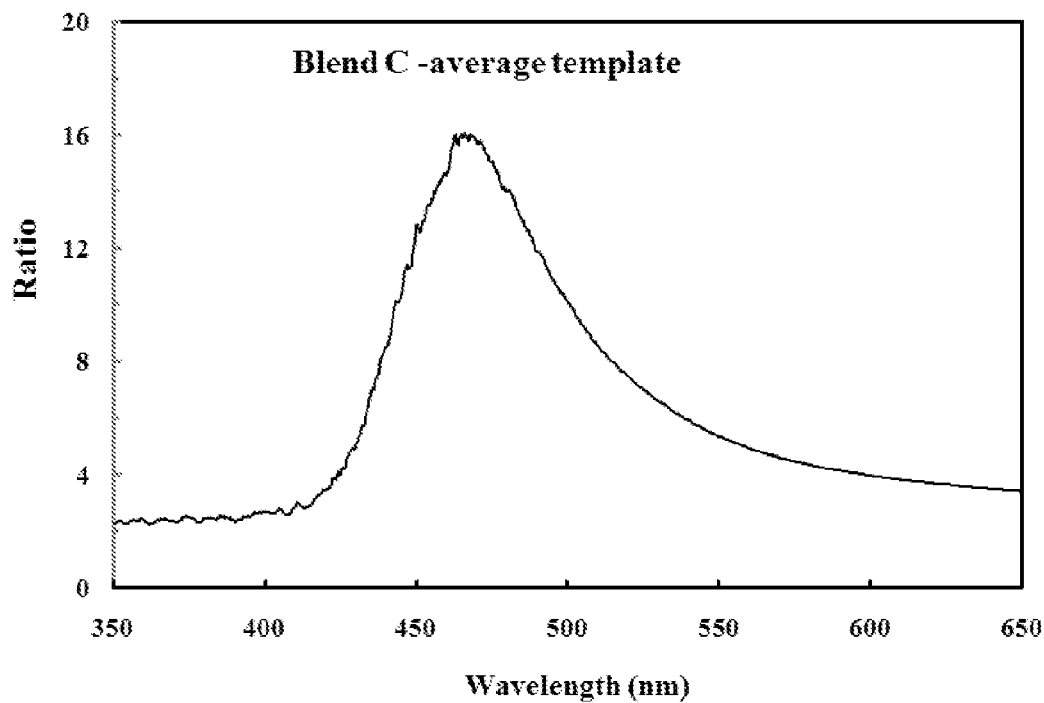
FIG. 6 shows an average of the R(λ) ratio for the four samples of Blend C shown in FIG. 5.

FIG. 6 shows the result of averaging the four responses for Blend C shown in FIG. 5 to produce a reference template $R_o(\lambda)$ to which further samples could be compared. The results of these comparisons are shown in FIGS. 7-10.

Figure 7:
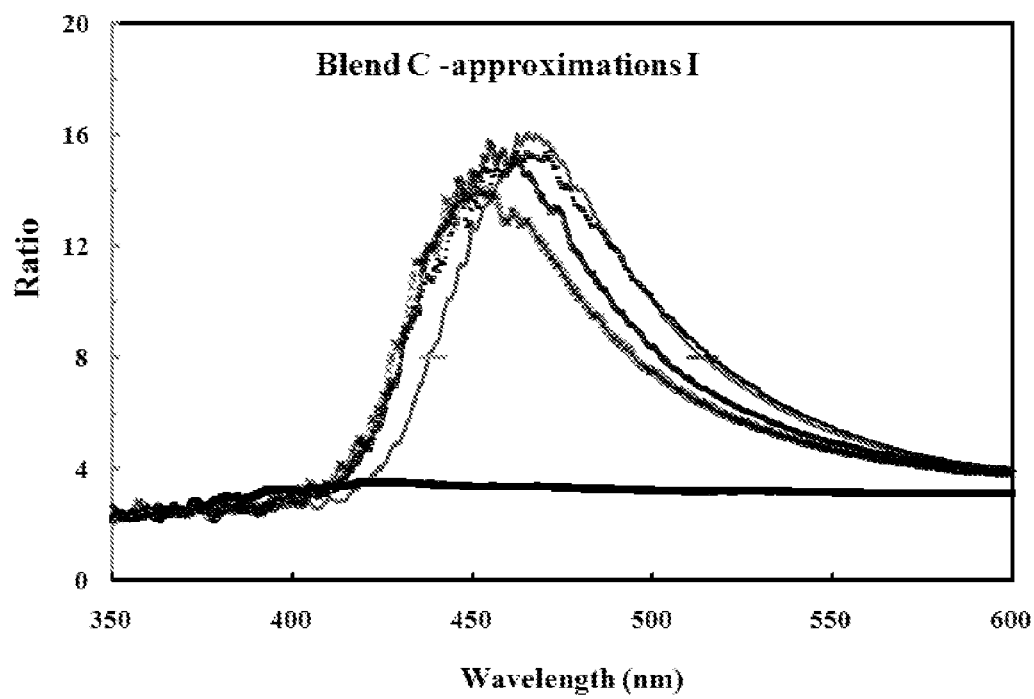
FIG. 7 shows a comparison of the R(λ) ratio for various samples with the average for Blend C shown in FIG. 6.

FIG. 7 shows overlaid graphs of the $R(\lambda)$ ratio for samples 1, 3 (squares), 4 (crosses) and 5 (dashes) of Table 1 compared to the Blend C average shown in FIG. 6 (solid line). This figure clearly shows how the method of the invention can be used to differentiate between Blend C whisky and "neutral spirit", the "neutral spirit" samples tested including a sample without additives as well as samples with caramel colours E150a, E150b or E150c added.

Figure 8:
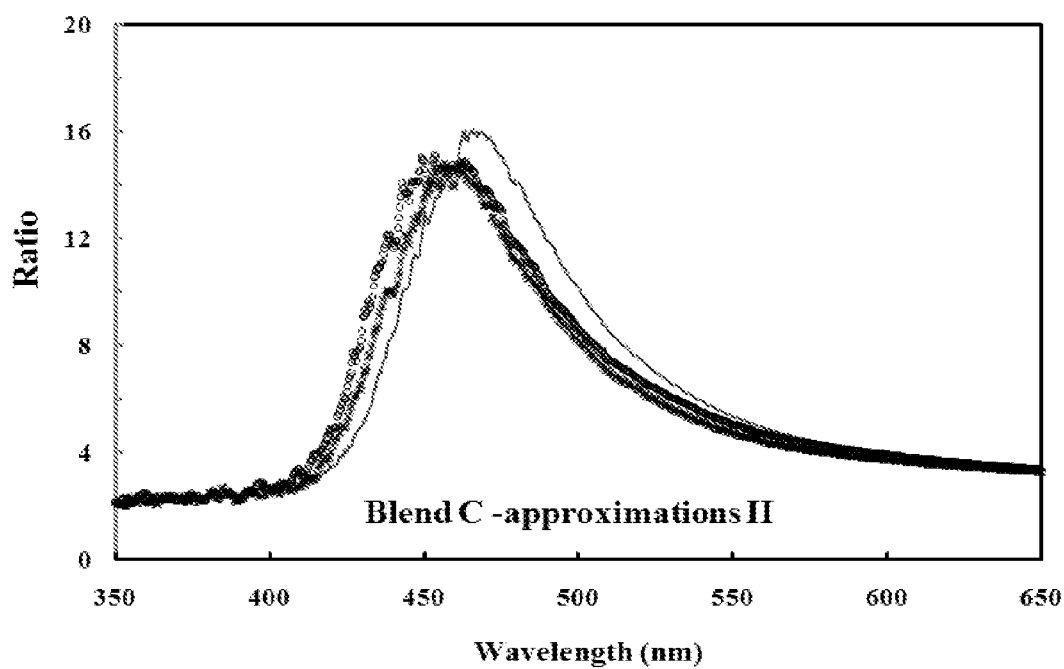
FIG. 8 shows a comparison of the R(λ) ratio for various samples with the average for Blend C shown in FIG. 6.

FIG. 8 shows overlaid graphs of the $R(\lambda)$ ratio for samples 12 (crosses) and 13 (circles) of Table 1 compared to the Blend C average shown in FIG. 6 (solid line). This figures demonstrates that the inventive method can also be used to distinguish between Blend C and sample 12, a mixture of 50% v/v of Blend C with 50% v/v of "neutral spirit" with E150a added as well as 6000 ppm methanol. The figure also shows that the method differentiates between Blend C and sample 13, a sample of Blend C subjected to "forced fade".

Figure 9:
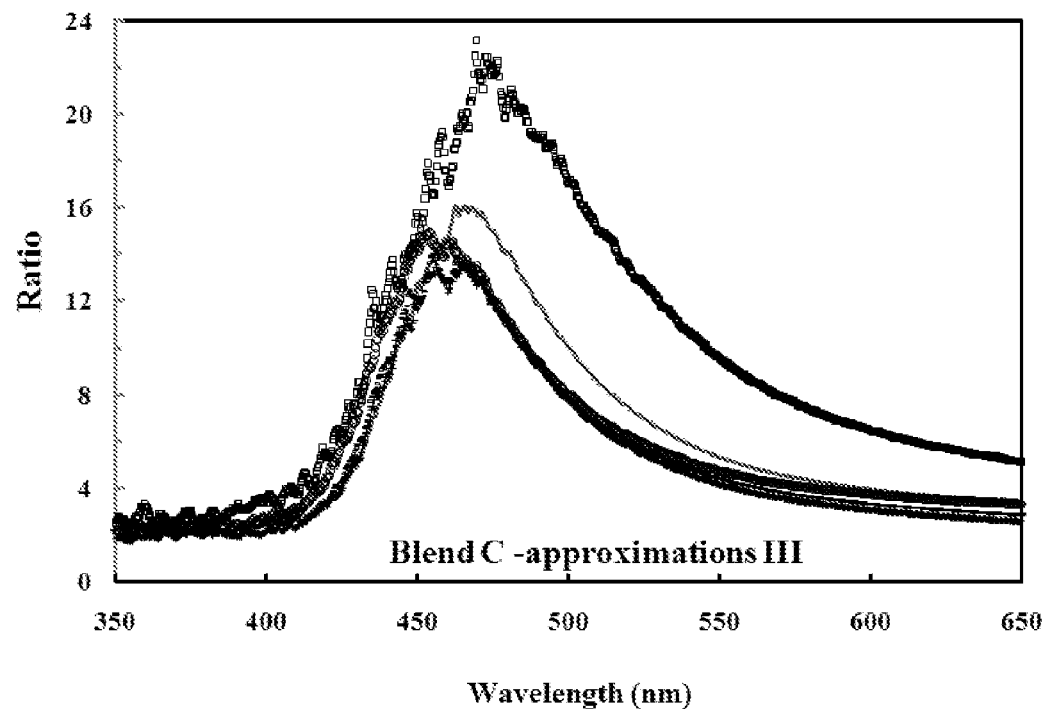
FIG. 9 shows a comparison of the R(λ) ratio for various samples with the average for Blend C shown in FIG. 6.

FIG. 9 shows overlaid graphs of the $R(\lambda)$ ratio for samples 6 (squares), 7 (dashes), 8 (crosses) and 9 (circles) of Table 1 compared to the Blend C average shown in FIG. 6 (solid line). This figure further demonstrates the sensitivity of the method of the invention. The Blend C average line can clearly be distinguished from the other samples. Sample 6 is "neutral spirit" with E150d added, samples 7-9 are mixtures at various ratios of Blend C and "neutral spirit" with E150a added.

Figure 10:
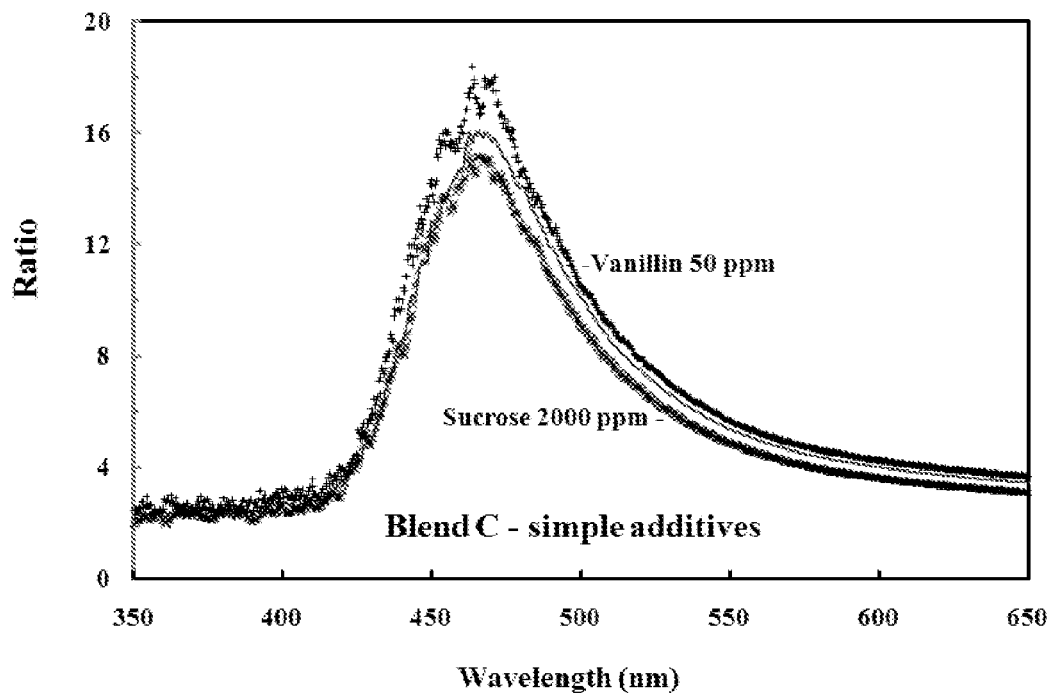
FIG. 10 shows a comparison of the R(λ) ratio for two adulterated samples with the average for Blend C shown in FIG. 6.

FIG. 10 shows overlaid graphs of the $R(\lambda)$ ratio for samples 10 (X crosses) and 11 (+ crosses) of Table 1 compared to the Blend C average shown in FIG. 6 (solid line). Again, the Blend C average can be distinguished from the samples. Sample 10 is Blend C with 2000 ppm sucrose and sample 11 is Blend C with 50 ppm vanillin. Despite these samples only being minor adulterations of Blend C, the method of the invention is sensitive enough to detect a difference between samples 10 and 11 and unadulterated Blend C.

Figure 11:
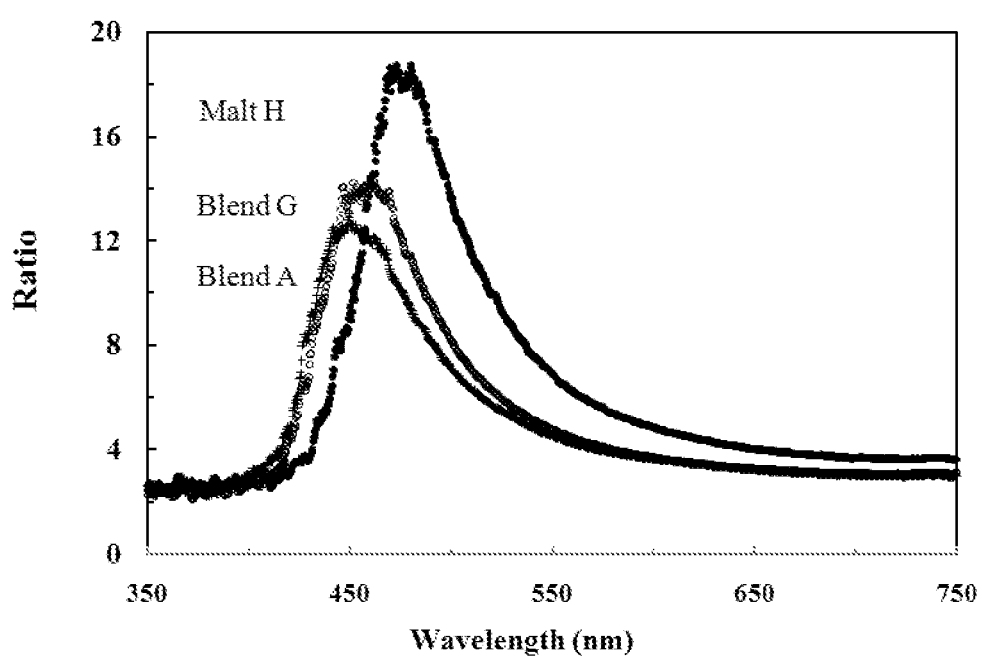
FIG. 11 shows overlaid measurements of the R(λ) ratio for two whisky blends and a malt whisky.

FIG. 11 describes the very significant differences—in maximum value of the ratio and the position of that maximum—for Blends A and G and Malt H. Samples A, G and H of Table 1 were analysed in the wavelength range 350-750 nm. FIG. 9 shows the sensitivity of the technique of this invention, the curves for each of the different whiskies analysed being significantly different.

The invention claimed is:

1. A method for analysing a liquid when inside a container in order to detect counterfeiting or adulteration of the liquid, the container being at least partially transparent to visible light, the method comprising the steps of:
   (a) measuring a first transmission spectrum through the container and the liquid at a first orientation of the container which defines a first optical path length through the liquid,
   (b) measuring a second transmission spectrum through the container and the liquid at a second orientation of the container which defines a second optical path length through the liquid, the second optical path length being different from the first optical path length, and the second spectrum at least partially overlapping with the first spectrum,
   (c) calculating the ratio ($R(\lambda)$) of the first and second spectral intensities at each wavelength in the area of overlap, and
   (d) comparing this ratio ($R(\lambda)$) to a reference measurement of the ratio for a non-counterfeit and unadulterated sample of the liquid being tested.

2. A method as claimed in claim 1, wherein the container comprises glass or plastic.

3. A method as claimed claim 1, wherein the liquid comprises ethanol.

4. A method as claimed in claim 3, wherein the liquid comprises one or more of cognac, brandy, bitters, dark rum, tequila, whisky or wine.

5. A method as claimed in claim 1, wherein the first and/or second spectra include measurements made across the wavelength range 350-500 nm.

6. A method as claimed in claim 5, wherein the wavelength range is 300-750 nm.

7. A method as claimed in claim 5, wherein the wavelength range is 350-850 nm.

8. A method as claimed in claim 1, wherein the reference measurement is stored electronically.

9. A method as claimed in claim 8, wherein the reference measurement is stored locally (with respect to the place of the first and second spectral measurements) or accessed remotely.

* * * * *